United States Patent
Boulanger

(10) Patent No.: US 11,517,703 B2
(45) Date of Patent: Dec. 6, 2022

(54) APPARATUS AND INSTALLATION FOR SUPPLYING A GAS MIXTURE TO A PATIENT

(71) Applicant: L'Air Liquide, Société Anonyme pour l'Etude et l'Exploitation des Procédés Georges Claude, Paris (FR)

(72) Inventor: Thierry Boulanger, Philadelphia, PA (US)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 441 days.

(21) Appl. No.: 16/824,474

(22) Filed: Mar. 19, 2020

(65) Prior Publication Data

US 2020/0297964 A1    Sep. 24, 2020

(30) Foreign Application Priority Data

Mar. 22, 2019    (FR) ...................................... 1902967

(51) Int. Cl.
*A61M 16/12*    (2006.01)
*A61M 16/20*    (2006.01)
(Continued)

(52) U.S. Cl.
CPC ........ *A61M 16/125* (2014.02); *A61M 16/105* (2013.01); *A61M 16/203* (2014.02);
(Continued)

(58) Field of Classification Search
CPC .............. A61M 16/125; A61M 16/105; A61M 16/203; A61M 2016/003;
(Continued)

(56) References Cited

U.S. PATENT DOCUMENTS 4,648,395 A * 3/1987 Sato .................... A61M 16/101
                                                 128/207.18
5,593,478 A * 1/1997 Hill .................... B01D 53/0446
                                                 96/111

(Continued)

FOREIGN PATENT DOCUMENTS

GB      2 553 790        3/2018
WO      WO 96 37176      11/1996
WO      WO 2004 073780   9/2004

OTHER PUBLICATIONS

French Search Report for corresponding FR 1902967, dated Jan. 31, 2020.

*Primary Examiner* — Colin W Stuart
*Assistant Examiner* — Douglas Y Sul
(74) *Attorney, Agent, or Firm* — Allen E. White

(57) ABSTRACT

An apparatus (1) for supplying a gas mixture to a patient, having a gas inlet line (30) with a gas inlet orifice (30*a*) that splits into a first gas line (31) and a second gas line (32); at least one permeation module (33) arranged on the second gas line (32), the said permeation module (33) having a feed port (33*a*) in fluidic communication with the second gas line (32), a retentate port (33*b*) and a permeate port (33*c*); a third gas line (34) in fluidic communication with the retentate port (33*b*) of the permeation module (33); a fourth gas line (35) in fluidic communication with the permeate port (33*c*) of the permeation module (33), and coupling fluidically to the said first gas line (31); and a source (360) of air in fluidic communication with the first gas line (31) and the fourth gas line (35).

11 Claims, 1 Drawing Sheet

(51) Int. Cl.
*A61M 16/10* (2006.01)
*A61M 16/00* (2006.01)

(52) U.S. Cl.
CPC ............... *A61M 2016/003* (2013.01); *A61M 2016/1025* (2013.01); *A61M 2202/0208* (2013.01); *A61M 2202/0283* (2013.01); *A61M 2205/07* (2013.01); *A61M 2205/50* (2013.01)

(58) Field of Classification Search
CPC .. A61M 2016/1025; A61M 2202/0283; A61M 2202/0208; B01D 2053/224; B01D 2256/12; B01D 2259/4533
See application file for complete search history.

(56) References Cited

U.S. PATENT DOCUMENTS

| | | | | |
|---|---|---|---|---|
| 5,893,275 | A * | 4/1999 | Henry | F25J 3/04636 |
| | | | | 62/911 |
| 7,955,294 | B2 * | 6/2011 | Stenzler | A61M 16/122 |
| | | | | 604/23 |
| 2010/0031960 | A1 * | 2/2010 | Knight | A61M 16/161 |
| | | | | 128/204.23 |
| 2012/0247329 | A1 * | 10/2012 | Hilbig | A61M 16/10 |
| | | | | 96/10 |
| 2013/0177657 | A1 * | 7/2013 | Hilbig | A61K 33/00 |
| | | | | 422/120 |
| 2013/0340753 | A1 * | 12/2013 | Weiszl | G05D 11/132 |
| | | | | 128/203.14 |
| 2014/0345609 | A1 * | 11/2014 | Whitcher | C01B 13/0259 |
| | | | | 128/202.26 |
| 2017/0120085 | A1 * | 5/2017 | Givens | B01D 53/1493 |

* cited by examiner

APPARATUS AND INSTALLATION FOR SUPPLYING A GAS MIXTURE TO A PATIENT

CROSS REFERENCE TO RELATED APPLICATIONS

This application claims the benefit of priority under 35 U.S.C. § 119 (a) and (b) to French Patent Application No. 1902967, filed Mar. 22, 2019, the entire contents of which are incorporated herein by reference.

BACKGROUND

The present invention relates to an apparatus and an installation for supplying a patient with a medical gas mixture, notably a mixture of gas containing nitrous oxide and oxygen, particularly a ternary mixture essentially made up of nitrous oxide, oxygen and nitrogen.

Nitrous oxide, $N_2O$, is a therapeutic gas which has analgesic (i.e. pain-reducing) and anxiolytic (i.e. stress-reducing) properties which take effect in the minutes following administration, and return fairly rapidly to the initial state when administration is interrupted. In addition, $N_2O$ is safe, has limited side effects, and is not metabolized.

It is generally administered at a high concentration, for example around 70% balanced with 30% oxygen ($O_2$) (mol %) at the start of an anaesthesia procedure, before more powerful anaesthetics are introduced. In that case, a source of pure medical $N_2O$, from a cylinder or a wall outlet, is used.

More commonly, it is used in childbirth in clinics, or else in dental practices, to facilitate care-giving. For these applications, which require a less powerful analgesic effect, a cylinder containing a medical-quality premix made up of 50% $N_2O$ and 50% $O_2$ (mol %) is used.

Now, long-term and repeated administration of this type of premix may pose problems.

Specifically, the high, 50 mol %, oxygen content may give rise to repeated instances of hyperoxia, which may have a negative effect on the condition of the patient after treatment, for example if the said patient is suffering with a comorbidity such as chronic cardiac insufficiency or chronic obstructive pulmonary disease.

Ideally, the oxygen concentration therefore needs to be set to the minimum in order to avoid any situation of hypoxemia that may occur during or after the end of the treatment because of the properties of $N_2O$, typically an oxygen concentration generally of the order of 30 mol %.

Now, creating a gas mixture containing $N_2O$ and such an oxygen concentration is not as simple as it might appear.

Therefore, the problem is that of being able to create a ternary mixture essentially containing $N_2O$, $O_2$ and $N_2$, while controlling the $O_2$ concentration, for example a fixed content of 30 mol %, but while at the same time offering the possibility to vary the $N_2O$ concentration while limiting the number of pressurized-gas sources, namely cylinders or other gas containers, used, preferably to a single cylinder or the like containing a non-hypoxic premix that meets the requirements for home use, namely use in the patient's home.

SUMMARY

One solution of the invention therefore relates to an apparatus for supplying a gas mixture to a patient, also referred to as a gas mixture generator, comprising:

a gas inlet line comprising a gas inlet orifice that splits into a first gas line and a second gas line, at least one permeation module arranged on the second gas line, the said permeation module comprising a feed port in fluidic communication with the second gas line, a retentate port and a permeate port, a third gas line in fluidic communication with the retentate port of the permeation module, a fourth gas line in fluidic communication with the permeate port of the permeation module, and coupling fluidically to the said first gas line, and a source of air in fluidic communication with the first gas line and the fourth gas line.

In the context of the present invention:

the percentages (%) are molar percentages (mol %), the air is considered to be made up of a mixture of oxygen (approximately 20 to 21%) and of nitrogen (approximately 78%), i.e. an $O_2/N_2$ mixture. The other constituents that might be present (Ar, CO2, etc.) are considered to be negligible (<2% approximately) and treated as being unavoidable impurities.

Depending on the embodiment considered, the gas mixture supply apparatus according to the invention may comprise one or more of the following features:

the permeation module comprises a plurality of hollow fibres, the hollow fibres each comprise a peripheral wall forming a permeation membrane and an internal gas passage or lumen, the permeation module comprises several hundred hollow fibres arranged in parallel, preferably at least one thousand hollow fibres, the permeation module comprises a gas feed port in fluidic communication with the second line and via which the feed gas mixture coming from the second line arrives, the permeation module further comprises a retentate port in fluidic communication with the third gas line and from whence part of the feed gas re-emerges from the permeation module with retention, i.e. from whence the compound (or compounds) not permeating through the membranes of the hollow fibres re-emerge(s), a permeate port in fluidic communication with the fourth gas line and from whence part of the gas having permeated re-emerges from the permeation module, i.e. from whence the compound (or compounds) permeating through the membranes of the hollow fibres re-emerge(s), the feed port is in fluidic communication with a first chamber of the permeation module, also referred to as upstream chamber or feed chamber, the permeation module moreover comprises a second chamber, also referred to as downstream chamber or retentate chamber, comprising the retentate port, the permeation module moreover comprises a third chamber, also referred to as intermediate chamber or permeate chamber, comprising the permeate port, the hollow fibres are arranged mainly in the third chamber, the first gas line comprises a first proportional solenoid valve and a first flow sensor, the first proportional solenoid valve and the first flow sensor together define a mass flow controller, the first proportional solenoid valve and the first flow sensor are electrically powered and controlled by an electronic control board and operated by a microcontroller of the electronic control board, the second gas line comprises a second proportional solenoid valve, the third gas line comprises a pressure sensor and a third proportional solenoid valve, i.e. the pressure sensor has its pressure tapping fluidically connected to the third gas line, the fourth gas line comprises a second flow sensor and a first oxygen sensor, the first flow sensor and/or the second flow sensor are mass-flow sensors, the source of air comprises an air pump fluidically connected to the atmosphere, it further comprises a control unit with a microcontroller, the control unit with microcontroller comprises the electronic board; for preference, the microcontroller is arranged on the electronic board, it comprises control means of the man-machine interface (MMI) type, that can be actuated by the user, for example a keyboard or a touch-screen preferably electronically connected to the control board, it further comprises electrical power supply means, the electrical power supply means comprise one or more batteries, notably rechargeable batteries, the electrical power supply means comprise an electric power cord fitted with a plug for connection to the mains supply (110/220V) or the like, it further comprises an external shell or casing, the first gas line and the fourth gas line meet, i.e. are fluidically connected to one another, to form a fifth gas line or common line, the source of air is in fluidic communication with the fifth gas line, the source of air is in fluidic communication with the fifth gas line via a sixth gas line that carries the air coming from the air source, typically an air pump, the sixth gas line comprises a third flow sensor, the fifth gas line and the sixth gas line meet, i.e. are fluidically connected to one another, to form a seventh gas line or main line, the seventh gas line comprising a second oxygen sensor and/or a nitrous-oxide sensor.

Furthermore, the invention also relates to an installation for creating and supplying a gas mixture, comprising:

a gas mixture supply apparatus according to the invention, a source of gas, such as a container of gas containing a gas premix with several ingredients, preferably an $N_2O/O_2$ premix, the said source of gas being fluidically connected to the apparatus to supply the said apparatus with a gas premix, and a patient circuit comprising a respiratory interface, such as a respiratory mask, the said patient circuit being fluidically connected to the apparatus in order to receive a gas mixture supplied by the said apparatus.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DETAILED DESCRIPTION OF PREFERRED EMBODIMENTS

Figure 1:
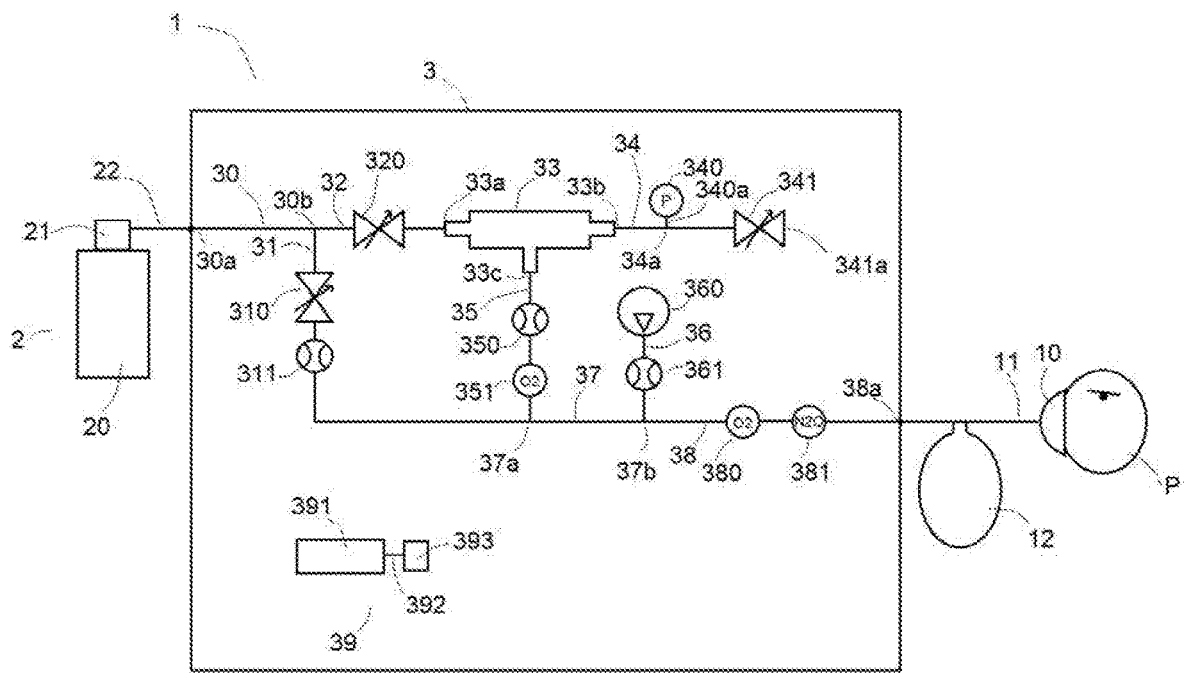
FIG. 1 schematically depicts one embodiment of an installation for creating and supplying a gas mixture, comprising a medical apparatus for supplying a gas mixture to a patient according to the invention, and FIG. 2 schematically depicts one embodiment of a permeation module of the apparatus of FIG. 1.

FIG. 1 schematically depicts one embodiment of an installation for creating and supplying a gas mixture 1, 2, 11 comprising a medical apparatus 1 for supplying a gas mixture to a patient, also referred to as a gas mixture generator according to the invention, a source of gas 2, such as a gas container, containing a gas premix with several ingredients, preferably an $N_2O/O_2$ premix, and a patient circuit 11.

The medical apparatus 1 for supplying gas, or gas mixture generator 1 of the invention, comprises an external shell or casing 3 comprising an internal inlet line 30 fluidically connected to the gas source 2 containing a gas premix, in this instance a medical-quality equimolar mixture of 50% $N_2O$ and 50% $O_2$, referred to as an $N_2O/O_2$ mixture.

The source of $N_2O/O_2$ mixture 2 here is a gas cylinder 20 containing this premix at a high pressure, for example up to 250 bar abs or more. A pressure regulator 21, preferably having pressure-reducing means, namely a valve with a built-in regulator, is mounted at the outlet of the cylinder 20 and delivers gas at a constant pressure for example of 5 bar abs, which is fed to the inlet port 30a of the inlet line 30, preferably via a flexible line 22 or the like.

The gas mixture generator 1 of the invention further comprises an outlet port 38a fluidically connected to the patient circuit 11 creating a fluidic connection between the outlet port 38a of the ternary gas mixture generator 1 and a respiratory interface 10, for example a respiratory face mask, used to supply a respiratory gas mixture to a patient P, namely a ternary mixture essentially containing $N_2O$, $O_2$ and $N_2$, the other gas species potentially present being considered to be negligible.

The gas supplied by the source 2 of $N_2O/O_2$ mixture passes in the gas mixture generator 1 between the inlet port 30a and the outlet port 38a inside an internal gas circuit comprising several gas lines 30, 31, 32, 35, 37 as explained hereinafter.

The patient circuit 11 comprises a gas reservoir 12 which acts as a reserve of respiratory gas for the patient P.

The constant supply of gas supplied by the generator 1, i.e. the gas flow rate desired, is regulated by the user, for example a doctor, to respond to the per-minute ventilation needs of the patient P, for example a gas flow rate of 10 l/min.

When the patient P inhales (i.e. in the inspiration phase), the gas reservoir 12 meets the instantaneous demand of the said patient P by supplying him with the quantity of respiratory gas which he needs, whereas when the patient P exhales (i.e. in the expiration phase), the gas reservoir 12 is filled once again with fresh gas coming from the generator 1.

Furthermore, it must be emphasized that all the electromechanical parts of the generator 1 of the invention, such as the solenoid valves, are powered and controlled by a control unit 39, also referred to as the operating unit or operating means, which typically comprises control means 393 of the man-machine interface (MMI) type, which can be actuated by the user, for example a keyboard or a touch-screen, which is also electronically connected to a control board 391, via a suitable electrical connection 392.

The control board 391 is designed or configured to power the various electromechanical components of the mixture generator 1. It incorporates a control unit, typically one (or several) microcontrollers, allowing control and/or analysis of the signals of the various electromechanical components of the generator 1, particularly one or more valves, sensors, etc.

Furthermore, the inlet line 30 of the gas mixture generator 1 of the invention splits, onwards from a branch point 30*b*, into two distinct lines, namely a first line 31 and a second line 32 which are in fluidic communication with the inlet line 30.

The first line 31 comprises, arranged in series, a first proportional solenoid valve 310 and a first flow sensor 311 together defining a mass flow controller. These are powered and controlled by the control board 391 and operated by the microcontroller of the control board 391.

In response to an action by the user via the control means 393, the microcontroller 394 may determine a flow rate setpoint Q and control the proportional solenoid valve 310 in such a way that the flow rate circulating through the first line 31, measured by the flow sensor 311, is equal to the said flow rate setpoint Q.

For example, it is possible to choose the mass flow controller comprising a first proportional solenoid valve 310 and a first flow sensor 311 from the SFC series available from Sensirion.

Similarly, a second proportional solenoid valve 320 is arranged in the second line 32 which supplies gas to the feed port 33*a* of a module for separating gas by permeation, also referred to as a permeation module 33.

Figure 2:
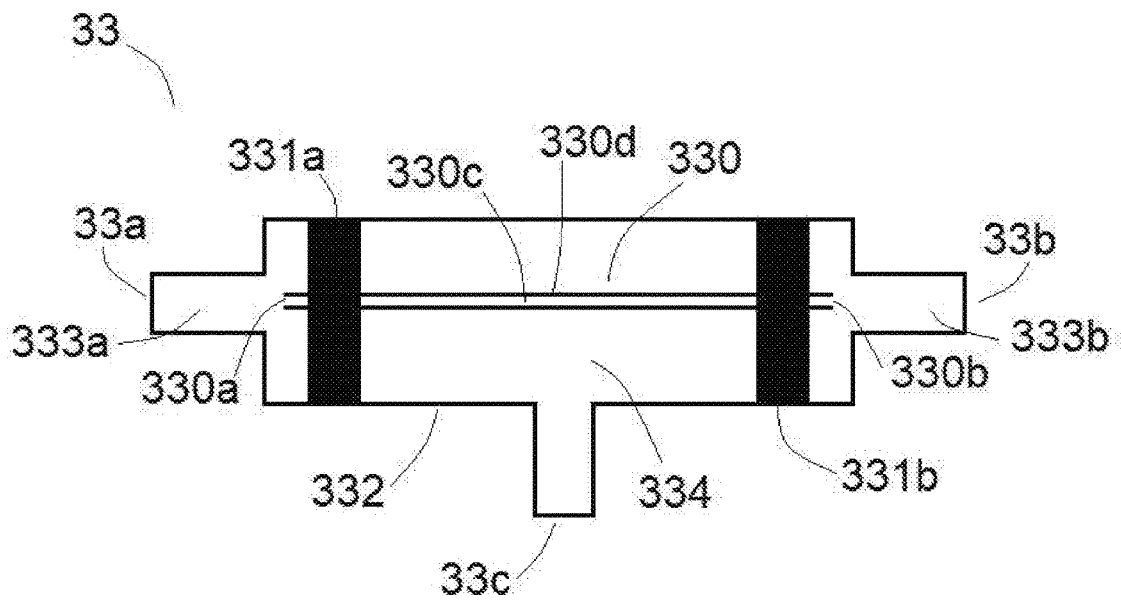

As depicted in FIG. 2, the permeation module 33 of the apparatus 1 comprises an external housing 332 forming a casing made of rigid material, for example of steel or of polymer, for example of PEEK type.

The external housing 332 of the permeation module 33 has three ports, namely the feed port 33*a* via which the feed gas mixture coming from the second line 32 arrives, a retentate port 33*b* from whence part of the feed gas re-emerges from the permeation module 33 (i.e. with retention, that is to say without having been permeated), and a permeate port 33*c* from whence part of the gas that has been permeated re-emerges from the permeation module 33.

The feed port 33*a* opens into a first chamber 333*a* of the permeation module 33, also referred to as upstream chamber or feed chamber. The permeation module 33 moreover comprises a second chamber 333*b*, also referred to as downstream chamber or retentate chamber, comprising the retentate port 33*b*, and a third chamber 334, also referred to as intermediate chamber or permeate chamber, comprising the permeate port 33*c*.

Arranged inside the permeation module 33 are hollow fibres 330. Each hollow fibre 330 has an internal canal or lumen 330*c* in which the gas mixture can circulate, and is delimited by a peripheral membrane 330*d*, namely a membrane that constitutes the peripheral wall of each hollow fibre 330.

Each hollow fibre 330 therefore has a tubular overall structure and forms or constitutes a membrane for separation by permeation. More specifically, the peripheral membrane 330*d* comprises a wall formed of a thin layer of material, typically a silicone-based material such as PDMS, a few microns thick.

Each hollow fibre 330 is held mechanically by seals 331*a*, 331*b*, for example plugs or the like, that provide a perfect seal between the first, second and third chambers 333*a*, 333*b* and 334 of the permeation module 33. The seals may for example be made of polyurethane.

The gas mixture coming from the second line 32 and fed to the chamber 333*a* of the permeation module 33 then enters the lumen 330*c* of each hollow fibre 330, entering it via a proximal end 330*a* in fluidic communication with the upstream chamber 333*a* of the permeation module 33.

The composition of the hollow fibres 330, namely its peripheral membrane 330*d*, is chosen to allow the selective separation, by permeation, of one (or more) gaseous species or compound(s) present in the feed gas mixture circulating along the lumen of the said hollow fibre 330.

Stated differently, a given molecule is able to pass by permeation across the membrane 330*d* of each fibre 330 and therefore pass from the internal canal or lumen 330*c* of each hollow fibre 330 to the third chamber 334 of the permeation module 33, before exiting same via the permeate port 33*c*. The number of molecules entering each hollow fibre 330 and crossing through the membrane 330*d* is dependent on the properties of this external membrane 330*d* and on the pressure gradient between the internal canal 330*c* of the hollow fibre 330 and the third chamber 334 of the permeation module 33. The higher this pressure gradient, the more easily the molecule is able to cross through the membrane 330*d* of each fibre 330.

The membrane 330*d* also exhibits higher selectivity for one compound of the mixture, for example for the nitrous oxide, so as to favour the permeation of this gaseous compound over the others. For example, the $N_2O/O_2$ selectivity of PDMS is 8:1, which means to say that the rate of permeation of the $N_2O$ molecules across the membrane 330*d* is 8 times higher than that of the $O_2$ molecules. PDMS is therefore suitable for the separation, by permeation, of the molecules of $N_2O$ of a mixture containing the compounds $O_2$ and $N_2O$. Of course, materials other than PDMS may be used to form the membrane 330*d* of each hollow fibre 330 provided that their selectivity is suitable, namely is suited to the desired separation.

So, assuming that 1 unit of feed gas (e.g. equimolar 50% $N_2O/50\%\ O_2$ mixture) enters the permeation module 33, and that there is a pressure gradient between the lumen 330*c* of each hollow fibre 330 and the third chamber 334, a proportion 1 of the feed gas will cross through the external membrane 330*d*, that is to say the permeate. The rest, i.e. the retentate, which is equal to (1-β), will exit each hollow fibre 330 via its distal end 330*b*. Because of the higher selectivity of the external membrane 330*d* towards the species $N_2O$, the permeate flow rate 13 is enriched in $N_2O$ (i.e. contains up to around 90% $N_2O$) which crosses more easily through the external membrane 330*d*, whereas the retentate flow rate (1-β) is enriched in $O_2$.

As a preference, the permeation module 33 is made up of several hollow fibres 330, advantageously several hundred or several thousand fibres 330, or even hundreds of thousands of fibres 330, arranged in parallel with one another. Using a great many fibres 330 makes it possible to increase the separation capacity and obtain significant flow rates, notably for the permeate (β), typically a permeate flow rate ranging up to 10 l/min, or even higher. Such permeation modules 33 are available from the company Porogen.

As detailed in FIG. 1, the retentate port 33*b* of the permeation module 33 is fluidically connected to a third line 34 comprising a third proportional solenoid valve 341. A pressure sensor 340 is also provided between the retentate port 33*b* and the third proportional solenoid valve 341, and is fluidically connected to the third line 34 via a tapping 340*a*. The outlet orifice 341*a* of the proportional solenoid valve 341 opens to the ambient atmosphere and therefore allows the retentate gas coming from the separation module 33, for example oxygen in the case of the aforementioned equimolar N₂O/O₂ mixture, to be discharged thereto.

The measurement range of the pressure sensor 340 is comprised between 0 and 7 bar abs. It is possible for example to use the pressure sensor referenced MS5803-07BA available from TE Connectivity.

Similarly, the permeate port 33c of the permeation module 33 is connected to a fourth line 35 comprising a second flow sensor 350, preferably a mass-flow sensor, for example a sensor from the SFM series available from Sensirion, and a first oxygen sensor 351 capable of detecting O₂ concentrations comprised between 0 and 100%, for example a sensor of electrochemical type, e.g. OOM series from Envitec, or of paramagnetic type, e.g. Paracube series by Hummingbird.

The fourth line 35 therefore collects the gas that has permeated through the hollow fibres 330, particularly a gas rich in N₂O in the aforementioned case of an equimolar N₂O/O₂ mixture.

As visible in FIG. 1, the fourth line 35 connects fluidically to the first line 31 (at 37a) downstream of the first flow sensor 311 to form a common line or fifth line 37 fed with the respective gas flows coming from the first and fourth lines 31, 35.

Moreover, an air source 360, such as an air pump, for example a pump from the 1610 series available from the company Thomas, draws in ambient air and delivers it to a sixth line, referred to as the aspiration line 36, comprising a third flow sensor 361, preferably a mass-flow sensor. The line 36 is fluidically connected (at 37b) to the common line or fifth line 37.

Downstream of the connection point 37b there is a seventh line or main line 38 along which there flows the final gas mixture, containing the various gaseous compounds at the desired contents coming from the fifth and sixth lines 37, 36, namely a mixture of N₂O/O₂, of O₂ and of air, respectively, for example.

In order to ensure the correct composition for the gas mixture circulating along the main line 38, which is made up of N₂O, O₂ and N₂, for example, and conveyed towards the patient P via the patient circuit 11, two additional sensors are provided, these namely being a second oxygen sensor 380 similar to the first oxygen sensor 351, and a nitrous-oxide sensor 381. The nitrous-oxide sensor 381 is also capable of detecting a wide range of concentrations of N₂O, for example between 0 and 100%. Use may be made for example of the sensor referenced IRMA AX+ available from the company PhaseIn.

Furthermore, the medical apparatus 1 for supplying gas, or gas mixture generator 1 of the invention, further comprises electrical power supply means (not depicted), for example one or more batteries, notably rechargeable batteries, and/or an electric power cord fitted with a plug for connection to the mains supply (110/220V) or the like.

For a gas premix made up of 50% O₂ and 50% N₂O (mol %), the operation of the gas supply apparatus 1 or gas mixture generator of the invention is as follows.

An operator authorized to initiate the therapy, such as a healthcare practitioner, uses the control means 393 to set or adjust:

a continuous flow rate, $Q_{TOTAL}$, which corresponds to the per-minute ventilation of the patient and is delivered to the said patient via the patient circuit 11 and the respiratory interface 10. This continuous flow rate corresponds to the final flow rate that is to be generated by the mixture generator 1 of the invention.

and a desired final composition for a ternary gas mixture to be supplied to the patient P, the said desired final composition being defined by the nitrous-oxide content $C_{N2O}$ and oxygen content $C_{O2}$, the remainder being essentially nitrogen N₂.

It is also considered that:

$Q_{KAL}$: is the flow rate of the gas circulating along the first line 31 coming from the source 2 of premix, i.e. 50% N₂O and 50% O₂, $Q_{PERM}$: is the flow rate circulating along the fourth line 35, coming from the permeate port 33c of the permeation module 33, at a given N₂O concentration, $C_{N2OP}$, which relates to an O₂ concentration $C_{O2P}=(1-C_{N2OP})$, $Q_{AIR}$: is the flow rate of ambient air injected into the line 36 by the pump 360 having a composition of the order of 80% N₂ and 20% O₂.

The distribution of the flow rates $Q_{KAL}$, $Q_{PERM}$ and $Q_{AIR}$ (in l/min) then obeys the following equations:

$$Q_{KAL} = \frac{5 \cdot (1 - C_{O2P}) \cdot (C_{N2O} + C_{O2} - 0.2) - 4 C_{N2O}}{2 \cdot (1 - 2 \cdot C_{O2P})} \cdot Q_{TOTAL} \quad \text{Math 1}$$

$$Q_{PERM} = \frac{(3 \cdot C_{N2O} - 5 \cdot C_{O2} + 1)}{4 \cdot (1 - 2 \cdot C_{O2P})} \cdot Q_{TOTAL} \quad \text{Math 2}$$

$$Q_{AIR} = \frac{(1 - C_{N2O} - C_{O2})}{0.8} \cdot Q_{TOTAL} \quad \text{Math 3}$$

In this example:

$Q_{TOTAL}$ is set to 10 l/min,

The desired N₂O concentration, $C_{N2O}$, is 40%,

The desired O₂ concentration, $C_{O2}$, is 30%.

Thus:

$$Q_{KAL} = \frac{25 \cdot (1 - C_{O2P}) - 16}{2 \cdot (1 - 2 \cdot C_{O2P})} \quad \text{Math 4}$$

$$Q_{PERM} = \frac{7}{4 \cdot (1 - 2 \cdot C_{O2P})} \quad \text{Math 5}$$

$$Q_{AIR} = 3.75 \quad \text{Math 6}$$

As stated previously, the premix source 2 comprises a pressure regulator 21 which provides a constant-pressure feed upstream of the proportional solenoid valves 310 and 320 (i.e. in the first and second lines 31, 32) of the order of 5 bar abs for example.

In order to generate the desired composition of mixture, the microcontroller 394 operates the proportional valve 320 to make it open, and this causes the gas circulating along the second line 32 to enter the permeation module 33 via its feed port 33a. A proportion β of the incoming flow rate is diverted to the permeate port 33c (after having passed across the membrane 330d of the hollow fibre 330) whereas the complement (1-β) of this same incoming flow rate leaves the permeation module 33 via its retentate port 33b. The ratio between the two flow rates β and (1-β) is determined by the properties of the hollow fibre 330 and the pressure gradient between the internal canal 330c of the said hollow fibre 330 and the chamber 334 of the permeation module 33. In order to maximize the proportion β of permeate (i.e. the N₂O concentration), the proportional solenoid valve 341 is operated by the microcontroller 394 in such a way as to maintain a stable pressure at the retentate port 33b. Because the retentate port 33b is connected fluidically to the third line 34, this is achieved by measuring the pressure obtaining in the third line 34 using the pressure sensor 340. The pressure received by the microcontroller 394 is used by it to define a command sent to the proportional valve 341. For example, a pressure of 3 bar may be desired.

Considering that the permeate port 33c (and therefore the third chamber 334 of the permeation module 33) is close to atmospheric pressure (i.e. 1 bar abs), it would appear that there is a pressure gradient between the internal canal 330c of the hollow fibre 330 and the said third chamber 334, and this allows effective separation of the gases, for example an $N_2O$ concentration in the permeate, $C_{N2OP}$, equal to approximately 75%, namely an $O_2$ concentration, $C_{O2P}$, equal to approximately 25%.

Because the permeate port 33c is connected fluidically to the fourth line 35 and because the latter comprises an oxygen sensor 351, the microcontroller 394 can determine that the $O_2$ concentration, $C_{O2P}$, of the gas circulating along the fourth line 35 is indeed approximately 25%, in order therefrom to deduce the values $Q_{KAL}$, $Q_{PERM}$: $Q_{KAL}$=2.75 l/min and $Q_{PERM}$=3.5 l/min.

To do that, the microcontroller 394 controls the opening of the second proportional valve 320 so as to obtain the desired flow rate $Q_{PERM}$ in the fourth line 35 by analysing the measurement from the flow sensor 350.

Thus, $Q_{PERM}$ is equal to 3.5 l/min.

At the same time, the first proportional solenoid valve 310 is operated by the microcontroller 394 which collaborates with the first flow sensor 311 to deliver a constant flow rate $Q_{KAL}$ of unmodified mixture containing 50% $N_2O$, 50% $O_2$, equal here to 2.75 l/min, which thus circulates along the first line 31.

In the event of a minor variation in the composition of the permeate circulating along the fourth line 35, for example as a result of ageing of the membrane or of differences between batches of the permeation module 33, the first oxygen sensor 351 makes it possible to determine the true concentration $C_{O2P}$ of the said permeate to be fed into the set of equations used for determining the flow rates $Q_{PERM}$ and $Q_{KAL}$.

The flow rate circulating along the fifth line 37 is therefore the sum of the flow rates circulating along the first line 31 ($Q_{KAL}$) and the fourth line 35 ($Q_{PERM}$), which join together at the branch point 37a.

In order to achieve the desired composition, the pump 360 is actuated by the microcontroller 394 in such a way that the third flow sensor 361 measures the desired flow rate $Q_{AIR}$, in this instance 3.75 l/min. This flow rate, circulating along the sixth line 36, mixes (at 37b) with the flow rate passing along the fifth line 37 to generate a total flow rate $Q_{TOTAL}$ in the main line 38 which is equal to that defined by the operator.

Furthermore, the oxygen sensor 380 and the nitrous-oxide sensor 381 inform the microcontroller 394 of the composition of the mixture so as to ensure that it is indeed that defined by the user, namely here that the $O_2$ concentration, $C_{O2}$, is 30% and the $N_2O$ concentration, $C_{N2O}$, is 40%. In such a case, the mixture circulating along the main line 38 leaves the mixture generator 1 via the outlet port 38a to be delivered to the patient P via the patient circuit 11, the gas reservoir 12 and the interface 10, as explained hereinabove.

In the event of there being too great a difference between the $O_2$ concentration, $C_{O2}$, and the $N_2O$ concentration, $C_{N2O}$, with respect to the setpoint set by the user, the microcontroller may decide to stop the therapy and inform the user through audible and/or visible signals, namely by triggering one (or more) alarm(s).

Bearing all the equations in mind, various flow rates $Q_{TOTAL}$ and various $N_2O$ or $O_2$ concentrations may be set by the user.

More specifically, by maintaining an $O_2$ concentration of 30% and a total flow rate $Q_{TOTAL}$ of 10 l/min, it is possible to determine the following flow rates:

$N_2O$ concentration=40%:
$Q_{KAL}$=2.75 l/min; $Q_{PERM}$=3.5 l/min; $Q_{AIR}$=3.75 l/min.
$N_2O$ concentration=50%:
$Q_{KAL}$=2.5 l/min; $Q_{PERM}$=5 l/min; $Q_{AIR}$=2.5 l/min.
$N_2O$ concentration=30%:
$Q_{KAL}$=3 l/min; $Q_{PERM}$=2 l/min; $Q_{AIR}$=5 l/min.

In other words, it is possible to define a different concentration of $N_2O$ according to the needs of the patient P and to generate a ternary mixture that keeps the oxygen level at a defined content.

The apparatus and the installation for supplying a gas mixture according to the invention are particularly well-suited to the home treatment of patients suffering from chronic pain.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. An apparatus (1) for supplying a gas mixture to a patient, comprising:
   a gas inlet line (30) comprising a gas inlet orifice (30a) that splits into a first gas line (31) and a second gas line (32),
   at least one permeation module (33) arranged on the second gas line (32), the said permeation module (33)

comprising a feed port (33a) in fluidic communication with the second gas line (32), a retentate port (33b) and a permeate port (33c), a third gas line (34) in fluidic communication with the retentate port (33b) of the permeation module (33), a fourth gas line (35) in fluidic communication with the permeate port (33c) of the permeation module (33), and fluidically connected to the first gas line (31), a source (360) of air in fluidic communication with the first gas line (31) and the fourth gas line (35), wherein the first gas line (31) and the fourth gas line (35) meet to form a fifth gas line (37), and the source of air (360) is in fluidic communication with the fifth gas line (37) via a sixth gas line (36) comprising a first flow sensor (361), and characterized in that the first gas line (31) and the fourth gas line (35) meet to form a fifth gas line (37), and the source (360) of air is in fluidic communication with the fifth gas line (37) via a sixth gas line (36) comprising an air flow sensor (361).

2. The apparatus (1) according to claim 1, characterized in that the permeation module (33) comprises a plurality of hollow fibres (330).

3. The apparatus (1) according to claim 1, characterized in that the first gas line (31) comprises a first proportional solenoid valve (310) and a second flow sensor (311).

4. The apparatus (1) according to claim 3, characterized in that the second gas line (32) comprises a second proportional solenoid valve (320).

5. The apparatus (1) according to claim 4, characterized in that the third gas line (34) comprises a pressure sensor (340) and a third proportional solenoid valve (341).

6. The apparatus (1) according to claim 3, characterized in that the fourth gas line (35) comprises a third flow sensor (350) and a first oxygen sensor (351).

7. The apparatus (1) according to claim 1, characterized in that the source (360) of air comprises an air pump fluidically connected to the atmosphere.

8. The apparatus (1) according to claim 1, characterized in that the apparatus further comprises a control unit (39) with a microcontroller.

9. The apparatus (1) according to claim 1, characterized in that the fifth gas line (37) and the sixth gas line (36) meet to form a seventh gas line (38), the seventh gas line (38) comprising a second oxygen sensor (380) and a nitrous-oxide sensor (381).

10. An installation (1, 2, 11) for creating and supplying a gas mixture (1, 2, 11), comprising:
a gas mixture supply apparatus (1) according to claim 1,
a source (2) of gas, containing a gas premix with several ingredients, the said source (2) of gas being fluidically connected to the apparatus (1) to supply the said apparatus (1) with the gas premix, and
a patient circuit (11) comprising a respiratory interface (10), the patient circuit (11) being fluidically connected to the apparatus (1) in order to receive a gas mixture supplied by the apparatus (1).

11. The installation (1, 2, 11) of claim 10, wherein the gas pre-mix comprises $N_2O$ and $O_2$.

* * * * *